US00PP32637P2

(12) United States Plant Patent
Koppe

(10) Patent No.: US PP32,637 P2
(45) Date of Patent: Dec. 15, 2020

(54) ***BEGONIA* PLANT NAMED 'KROUTYE01'**

(50) Latin Name: ***Begonia boliviensis* X *Begonia* x *tuberhybrida***
Varietal Denomination: KROUTYE01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 16/873,044

(22) Filed: Jan. 21, 2020

(51) Int. Cl.
*A01H 6/18* (2018.01)
*A01H 5/02* (2018.01)

(52) U.S. Cl.
USPC ..... Plt./343

(58) Field of Classification Search
USPC ..... Plt./343
See application file for complete search history.

(56) References Cited

PUBLICATIONS

PLUTO Plant Variety Database Jul. 21, 2020.*

* cited by examiner

*Primary Examiner* — Annette H Para
(74) *Attorney, Agent, or Firm* — C. A. Whealy

(57) ABSTRACT

A new and distinct cultivar of *Begonia* plant named 'KROUTYE01', characterized by its broadly upright to spreading and mounded plant habit; moderately vigorous to vigorous growth habit; moderately freely branching habit; dark greyed green-colored leaves; large single-type light yellow-colored flowers that are positioned above and beyond the foliar plane; and continuous flowering throughout the summer.

2 Drawing Sheets

Figure 1:
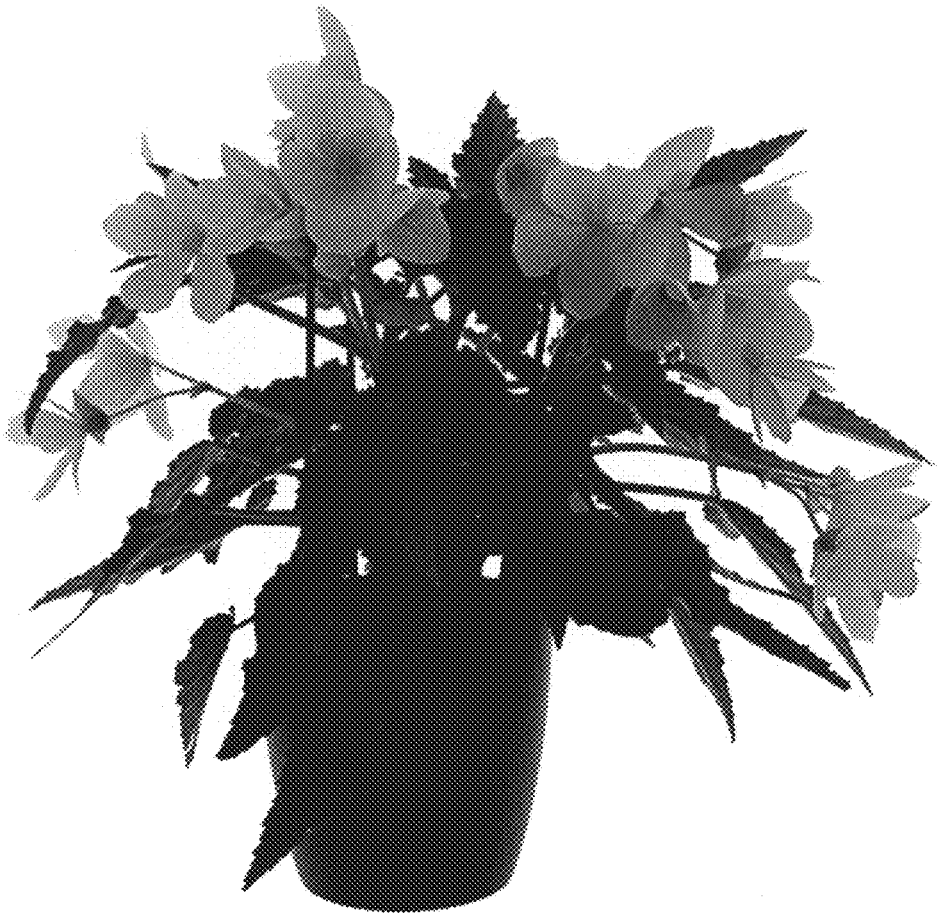

Botanical designation: *Begonia boliviensis* X *Begonia* x *tuberhybrida*.
Cultivar denomination: 'KROUTYE01'.

BACKGROUND OF THE INVENTION

The present invention relates to a new and distinct cultivar of *Begonia* plant, botanically known as *Begonia boliviensis* X *Begonia* x *tuberhybrida* and hereinafter referred to by the name 'KROUTYE01'.

The new *Begonia* plant is a product of a planned breeding program conducted by the Inventor in Ermelo, The Netherlands. The objective of the breeding program is to create new *Begonia* plants with uniform plant habit and numerous attractive flowers.

The new *Begonia* plant originated from a cross-pollination made by the Inventor in Ermelo, The Netherlands in September, 2015 of *Begonia boliviensis* 'Million Kisses Romance', not patented, as the female, or seed, parent with a proprietary selection of *Begonia* x *tuberhybrida* identified as code number KV11K1912-012, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in June, 2016.

Asexual reproduction of the new *Begonia* plant by terminal vegetative cuttings taken in a controlled greenhouse environment in Ermelo, The Netherlands since March, 2017 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KROUTYE01'. These characteristics in combination distinguish 'KROUTYE01' as a new and distinct *Begonia* plant:

1. Broadly upright to spreading and mounded plant habit.
2. Moderately vigorous to vigorous growth habit.
3. Moderately freely branching habit.
4. Dark green-colored leaves.
5. Large single-type light yellow-colored flowers that are positioned above and beyond the foliar plane.
6. Continuous flowering throughout the summer.

Plants of the new *Begonia* differ primarily from plants of the female parent, 'Million Kisses Romance', in the following characteristics:

1. Plants of the new *Begonia* are more freely flowering than plants of 'Million Kisses Romance'.
2. Plants of the new *Begonia* have larger and more open flowers than plants of 'Million Kisses Romance'.
3. Plants of the new *Begonia* and 'Million Kisses Romance' differ in flower color as plants of the new *Begonia* have light yellow-colored flowers whereas plants of 'Million Kisses Romance' have salmon orange-colored flowers.

Plants of the new *Begonia* differ primarily from plants of the male parent selection in the following characteristics:

1. Plants of the new *Begonia* are larger than plants of the male parent selection.
2. Plants of the new *Begonia* and the male parent selection differ in flower color as plants of the new *Begonia* have light yellow-colored flowers whereas plants of the male parent selection have white-colored flowers.

Plants of the new *Begonia* can be compared to plants of *Begonia boliviensis* X *Begonia* x *tuberhybrida* 'KROUTOR01', disclosed in U.S. Plant Pat. No. 26,248. In side-by-side comparisons conducted in Ermelo, The Netherlands, plants of the new *Begonia* differed primarily from plants of 'KROUTOR01' in flower color as plants of the new *Begonia* have light yellow-colored flowers whereas plants of 'KROUTOR01' have dark orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical plant of 'KROUTYE01' grown in a container.

Figure 2:
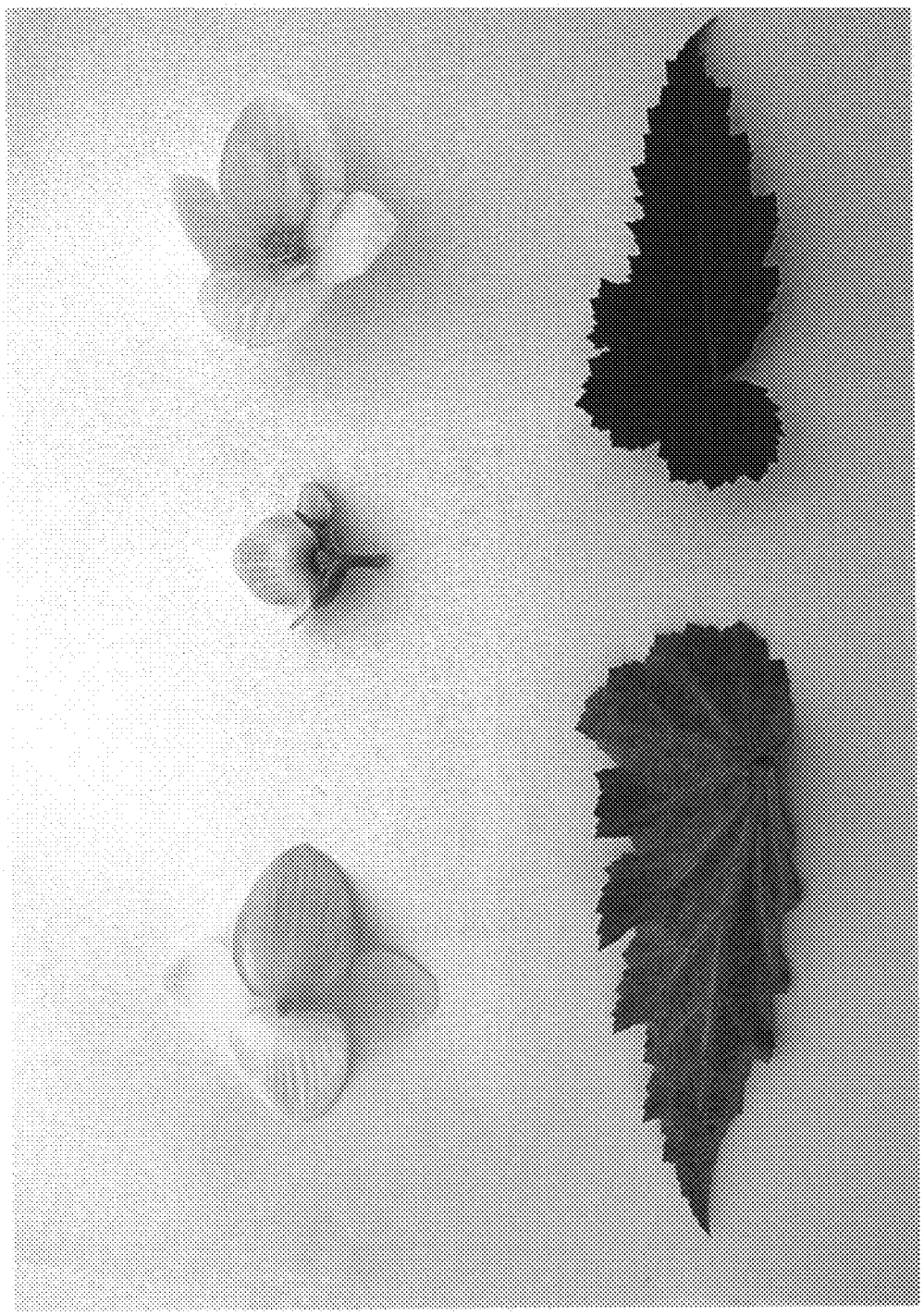

The photograph on the second sheet (FIG. 2 of 2) is a close up view of typical male flowers and leaves of 'KROUTYE01'.

DETAILED BOTANICAL DESCRIPTION

The aforementioned photographs and following observations and measurements describe plants grown during the late summer and autumn in 11-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were two months old when the photographs and description were taken. In the following description, color references are made to The Royal Horticultural Society Colour Chart, 2015 Edition, except were general terms of ordinary dictionary significance are used.

Botanical classification: *Begonia boliviensis* X *Begonia* x *tuberhybrida* 'KROUTYE01'.

Parentage:

*Female, or seed, parent.*—*Begonia* x *tuberhybrida* 'Million Kisses Romance', not patented.

*Male, or pollen, parent.*—Proprietary selection of *Begonia* x *tuberhybrida* identified as code number KV11H1912-012, not patented.

Propagation:

*Type.*—By terminal vegetative cuttings.

*Time to initiate roots, summer and winter.*—About 20 days at temperatures about 20° C.

*Time to produce a rooted young plant, summer and winter.*—About five weeks at temperatures about 20° C.

*Root description.*—Fine, fibrous; typically white to orange brown in color, actual color of the roots is dependent on substrate composition, water quality, fertilizer type and formulation, substrate temperature and physiological age of roots.

*Rooting habit.*—Freely branching; medium density; plants of the new *Begonia* have not been observed to form tubers to date.

Plant description:

*Plant habit and form.*—Broadly upright to spreading and mounded plant habit; flattened globular in overall plant shape.

*Growth habit.*—Moderately vigorous to vigorous growth habit and moderate growth rate; suitable for 9-cm and larger containers; under optimal environmental and cultural conditions, usually about eight weeks are required to produce proportional 11-cm potted plants from rooted cuttings.

*Branching habit.*—Moderately freely branching habit, about three basal branches each with about three secondary branches develop per plant; dense and bushy plant habit.

*Plant height, soil level to top of foliar plane.*—About 23.9 cm.

*Plant height, soil level to top of floral plane.*—About 27.1 cm.

*Plant width.*—About 41.5 cm.

*Lateral branches.*—Length: About 13.4 cm. Diameter: About 8 mm. Internode length: About 2.7 cm. Aspect: Erect to about 60° from vertical. Strength: Flexible, bending with the weight of the flowers. Texture and luster: Moderately pubescent; moderately glossy. Color, developing: Close to 144A; at the internodes, close to 183A. Color, developed: Close to 200B slightly tinged with close to 177A; with subsequent development, becoming closer to between N186C and 200A.

*Leaves.*—Arrangement: Alternate; simple. Length: About 16.5 cm. Width: About 6.4 cm. Shape: Narrowly ovate to lanceolate. Apex: Acute. Base: Oblique, lobes free. Margin: Dentate to serrate; moderately undulate. Texture and luster, upper surface: Sparsely pubescent; slightly velvety; moderately glossy. Texture and luster, lower surface: Moderately pubescent; slightly velvety; moderately glossy. Venation pattern: Pinnate. Color: Developing leaves, upper surface: Close to between 139A and N189A tinged with close to 203A. Developing leaves, lower surface: Close to 187B. Fully expanded leaves, upper surface: Darker than between NN137A and 147A; venation, close to 147A. Fully expanded leaves, lower surface: Close to 147B tinged with close to 183C to 183D; venation, close to 146B. Petioles: Length: About 6.4 cm. Diameter: About 4 mm. Texture and luster, upper and lower surfaces: Moderately pubescent; moderately glossy. Color, upper surface: Close to between 175A and 176A; proximally and distally, close to 183A. Color, lower surface: Close to 176A. Stipules: Quantity and appearance: Two leafy stipules positioned at base of the leaf. Length: About 7 mm. Width: About 6 mm. Shape: Deltoid to broadly ovate. Apex: Acute. Base: Broadly cuneate. Margins: Finely ciliate. Color, upper and lower surfaces: Close to 144B to 144C; venation, close to 144A.

Flower description:

*Flower form and flowering habit.*—Large rotate flowers arranged in axillary cymes; typically about five flowers per cyme, numerous cymes in flower simultaneously and about 100 flowers developing per plant; flowers face outwardly to slightly nodding and are positioned above and beyond the foliar plane.

*Natural flowering season*.—Plants flower continuously from the spring into the autumn in The Netherlands.

*Flower longevity*.—Individual flowers last about ten days on the plant; flowers not persistent.

*Fragrance*.—None detected.

*Inflorescence height* (*including peduncle*).—About 18.2 cm.

*Inflorescence diameter*.—About 13.4 cm.

*Flower buds, female flowers*.—Length: About 2.6 cm. Diameter: Ranging from about 0.8 cm to 2.2 cm. Shape: Ovate, flattened. Texture and luster: Smooth, glabrous; velvety; matte. Color: Close to 150D; towards the margins and apex, close to 154D.

*Flower buds, male flowers*.—Length: About 2.3 cm. Diameter: Ranging from about 0.8 cm to 2.2 cm. Shape: Ovate, flattened. Texture and luster: Smooth, glabrous; velvety; matte. Color: Close to 150D; towards the margins and apex, close to 154D.

*Female flowers*.—Diameter: About 7 cm by 7 cm. Depth: About 3.2 cm. Shape: Rotate, single. Tepals: Quantity and arrangement: About five arranged in two whorls. Length, inner whorl: About 3.8 cm. Length, outer whorl: About 3.9 cm. Width, inner and outer whorls: About 2.8 cm. Shape, inner whorl: Obovate. Shape, outer whorl: Ovate to obovate. Apex, inner whorl: Obtuse. Apex, outer whorl: Acute. Base, inner and outer whorls: Cuneate. Margin, inner and outer whorls: Entire, not undulate. Texture and luster, upper surface, inner and outer whorls: Smooth, glabrous; moderately velvety; matte. Texture and luster, lower surface, inner and outer whorls: Smooth, glabrous; moderately velvety; matte and proximally, slightly glossy. Color: When opening, upper surface, inner and outer whorls: Close to 4C. When opening, lower surface, inner and outer whorls: Close to between 2D and 4D. Fully opened, upper surface, inner and outer whorls: Close to 10C; venation, close to 154C; color does not change with development. Fully opened, lower surface, inner and outer whorls: Close to 8C to 8D; venation, close to 154C; color becoming closer to 38A with development. Tepaloids: None observed on female flowers.

*Male flowers*.—Diameter: About 9 cm by 7.7 cm. Depth: About 2.4 cm. Shape: Rotate, semi-double. Tepals: Quantity and arrangement: About four arranged in two whorls. Length, inner whorl: About 4.1 cm. Length, outer whorl: About 4.7 cm. Width, inner whorl: About 2.7 cm. Width, outer whorl: About 3.6 cm. Shape, inner whorl: Obovate. Shape, outer whorl: Ovate. Apex, inner and outer whorls: Obtuse. Base, inner and outer whorls: Cuneate. Margin, inner and outer whorls: Entire, not undulate. Texture and luster, upper surface, inner and outer whorls: Smooth, glabrous; moderately velvety; matte. Texture and luster, lower surface, inner and outer whorls: Smooth, glabrous; moderately velvety; moderately glossy. Color: When opening, upper surface, inner and outer whorls: Close to between 3C and 4C. When opening, lower surface, inner whorl: Close to 4C. When opening, lower surface, outer whorl: Close to 4C slightly tinged with close to 51D. Fully opened, upper surface, inner and outer whorls: Close to between 3C and 4C; venation, close to 11B; color becoming closer to between 8D and 18A to 18B and margins, close to 35C with development. Fully opened, lower surface, inner whorl: Close to 8C to 8D; venation, close to 11B; color does not change with development. Fully opened, lower surface, outer whorl: Close to 8C to 8D; venation, close to 11B; color becoming closer to 38A with development. Tepaloids: Quantity and arrangement: About eight arranged in a single whorl. Length: About 1.9 cm. Width: About 1 cm. Shape: Irregularly obovate. Apex: Obtuse to bluntly acute. Base: Narrowly cuneate to attenuate. Margin: Entire, not undulate. Texture and luster, upper and lower surfaces: Smooth, glabrous; slightly velvety; matte. Color: When opening, upper surface: Close to between 3C and 4C. When opening, lower surface: Close to 4C. Fully opened, upper surface: Close to 8A to 8B; venation, close to 8A to 8B; color does not change with development. Fully opened, lower surface Close to 8C; venation, close to 8A; color does not change with development.

*Flower bracts*.—Quantity and arrangement: Two positioned at the top of the peduncle. Length: About 1.1 cm. Width: About 1.2 cm. Shape: Orbicular. Apex: Obtuse. Base: Broadly cuneate. Margin: Finely ciliate. Texture and luster, upper and lower surfaces: Smooth, glabrous; slightly glossy. Color, upper and lower surfaces: Close to 144B to 144C.

*Peduncles*.—Length: About 9.5 cm. Diameter: About 4 mm. Angle: About 35° from lateral branch axis. Strength: Flexible, bending with the weight of the flowers. Texture and luster: Sparsely pubescent; moderately glossy. Color: Close to 172A; proximally, close to 173A and distally, close to 146D.

*Pedicels*.—Length: About 3.4 cm. Diameter: About 2 mm. Angle: About 40° from peduncle axis. Strength: Flexible, bending with the weight of the flowers. Texture and luster: Sparsely to moderately pubescent; glossy. Color, upper surface: Close to 175A. Color, lower surface: Close to 174A to 174B.

*Reproductive organs*.—Stamens (present on male flowers only): Quantity per flower: About 50. Filament length: About 5 mm. Filament color: Close to 154C. Anther shape: Obovate; basifixed. Anther size: About 1 mm by 2 mm. Anther color: Close to 13A. Pollen amount: Scarce. Pollen color: Close to 4D. Pistils (present on female flowers only): Quantity per flower: About six, fused in pairs. Pistil length: About 8 mm. Style length: About 5 mm. Style color: Close to 16A. Stigma diameter: About 4.5 mm. Stigma color: Close to 14A. Ovary color: Close to 145A to 145B; distally, close to 42D.

*Seeds and fruits*.—To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KROUTYE01' as illustrated and described.

* * * * *